(12) United States Patent
Sasaki et al.

(10) Patent No.: US 6,289,073 B1
(45) Date of Patent: *Sep. 11, 2001

(54) X-RAY CT APPARATUS (75) Inventors: Tomiya Sasaki; Hisashi Tachizaki, both of Tochigi (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,560

(22) Filed: Oct. 23, 1998

(30) Foreign Application Priority Data

Oct. 23, 1997 (JP) .............................. P09-291188

(51) Int. Cl.$^7$ .................................................. G01N 23/00
(52) U.S. Cl. ............................................................ 378/4
(58) Field of Search ........................................ 378/17, 4

(56) References Cited

U.S. PATENT DOCUMENTS

| | | | |
|---|---|---|---|
| 4,112,303 | * | 9/1978 | Brandt .................................... 378/17 |
| 4,750,195 | * | 6/1988 | Takahashi .............................. 378/17 |
| 5,448,607 | * | 9/1995 | McKenna ................................. 378/4 |
| 5,448,608 | * | 9/1995 | Swain et al. ............................. 378/4 |

* cited by examiner

Primary Examiner—Craig E. Church
(74) Attorney, Agent, or Firm—Oblon, Spivak, McClelland, Maier & Neustadt, P.C.

(57) ABSTRACT

An X-ray CT apparatus includes a frame 1 and a radiographic unit accommodated in the frame 1. The upper portion of the frame 1 is shaped to be generally semicircular. In this X-ray CT apparatus, almost electric components 9 are positioned in the lower part of the frame 1 collectively. Consequently, such a positioning of the electric components makes it easy to realize a shielding structure for the components against the electromagnetic noises. It is possible to arrange a power line 15 and a signal line 16 in a perfectly separated manner and reduce the wiring area and length of the lines 15, 16.

16 Claims, 11 Drawing Sheets

X-RAY CT APPARATUS

BACKGROUND OF THE INVENTION

1. Field of the Invention

The present invention relates to an X-ray CT apparatus which has a compact and lightweight structure in comparison with the conventional X-ray CT apparatus.

2. Description of Related Art

Figure 1:
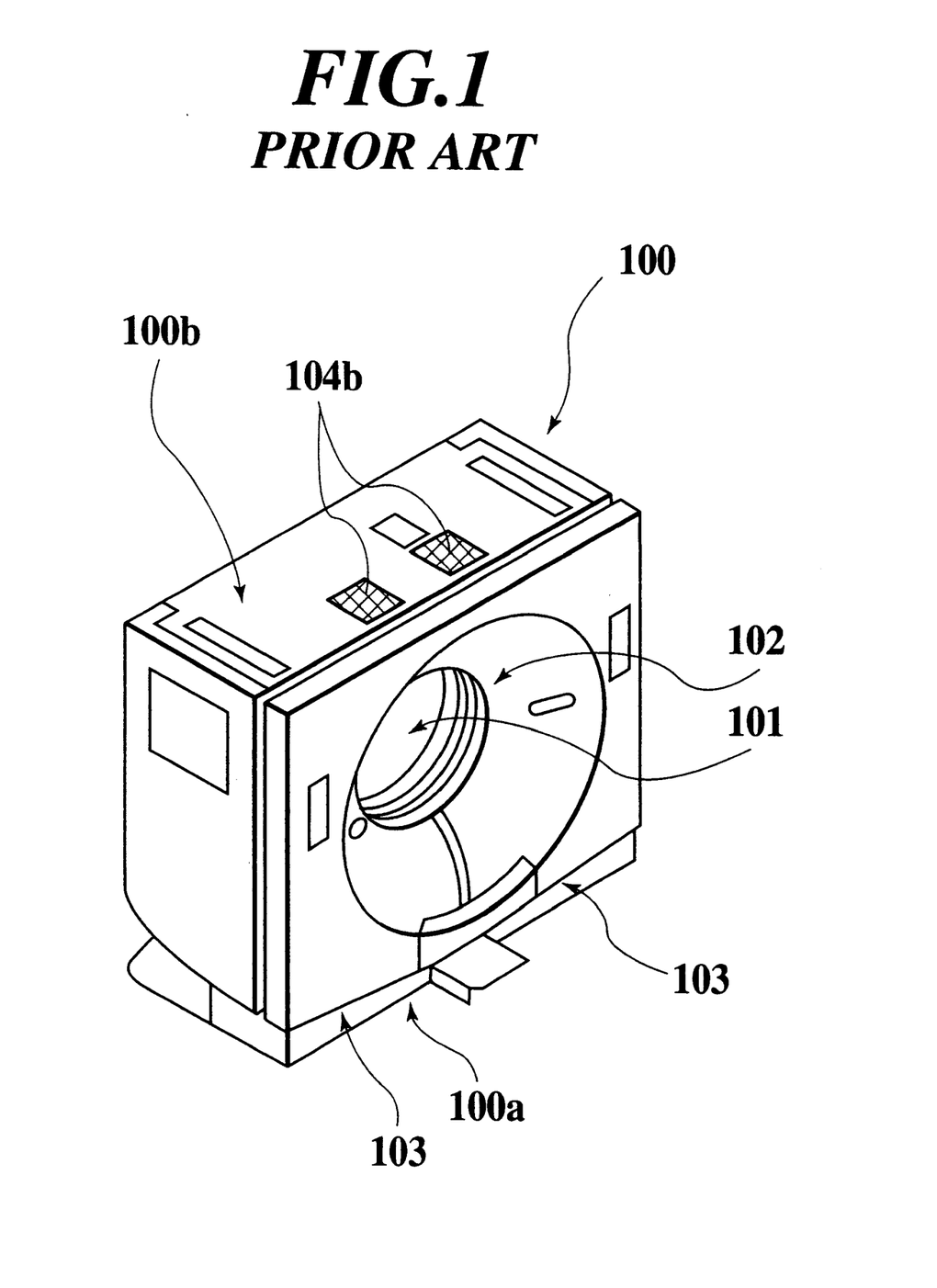
FIG. 1 is a perspective view of a conventional art X-ray CT apparatus.

There is a known X-ray CT apparatus of a so-called "helical-scanning" type, as shown in FIG. 1. The shown X-ray CT apparatus includes a frame 100 in the form of a box. Disposed at the center of the frame 100 is a radiographic port 101 into which a patient laid on a not-shown bed is to be inserted. About the radiographic port 101, an X-ray tube and an X-ray detector opposing thereto are adapted so as to rotate along the periphery of the port 101 together with a part of power processing components and signal processing components, providing a rotating part 102. In operation, by irradiating X-ray against the patient inserted into the radiographic port 101 while the rotating part 102 rotates, the X-ray apparatus is so constructed as to pick up an image of tomographic layer of a desired part of the patient. Further, the frame 100 is provided, on a bottom part 100a thereof, with a suction port 103. On an upper part 100b of the frame 100, cooling fans 104b are disposed to discharge air sucked through the suction port 103 for circulating the interior of the rotating part 102, thereby cooling down the X-ray tube and power circuits etc. which are heated by scanning.

Figure 2A:
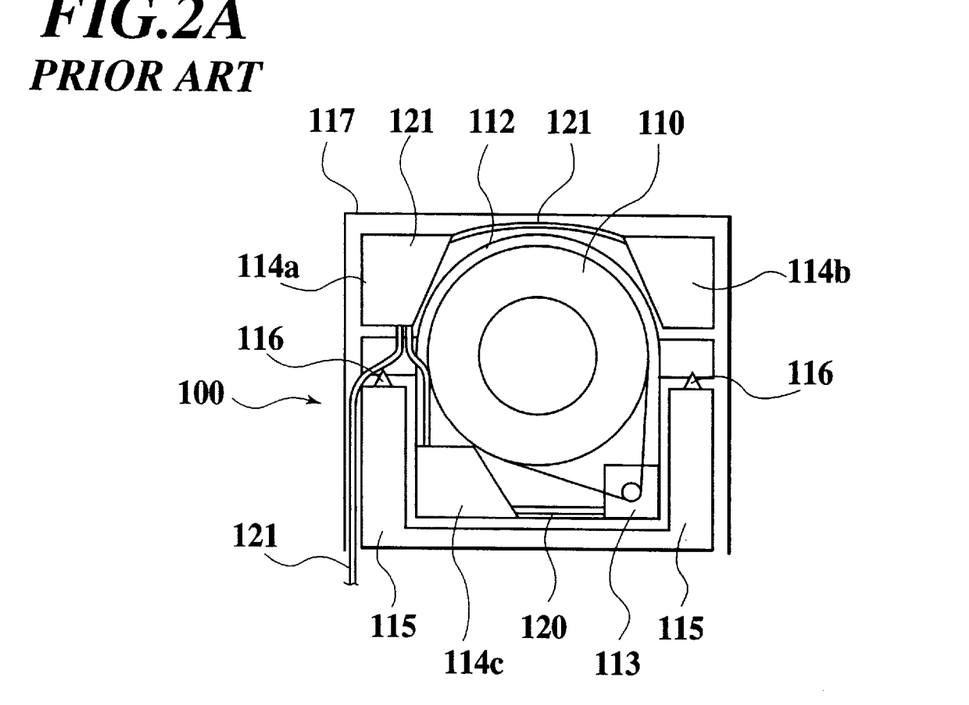
FIGS. 2A and 2B are cross sectional views of the X-ray CT apparatus of FIG. 1.
Figure 2B:
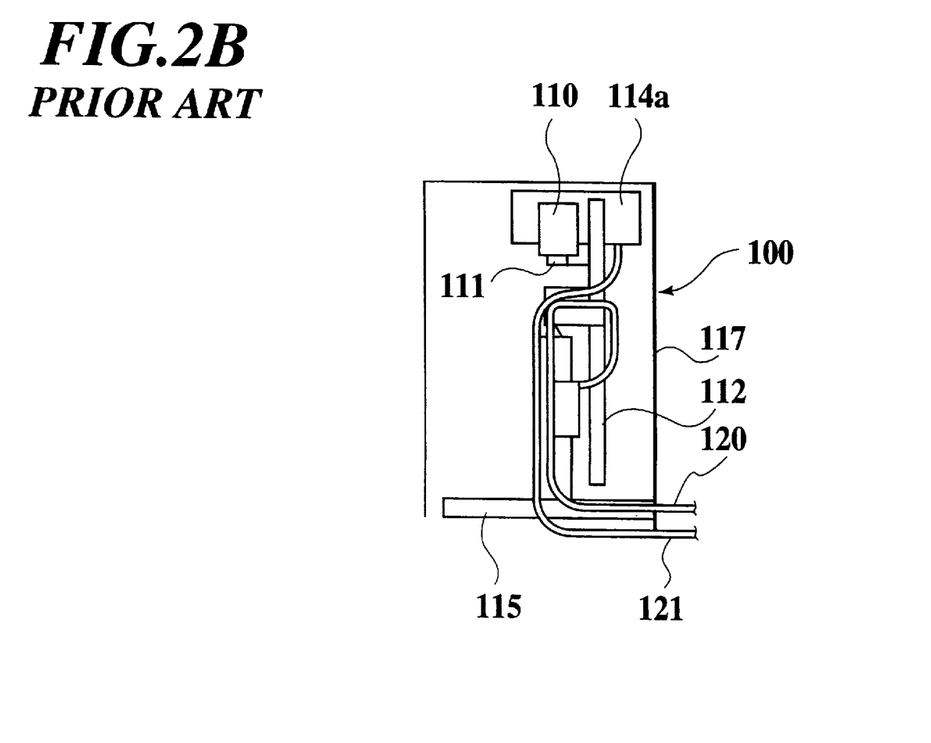

The interior constitution of the frame 100 are shown in FIGS. 2A and 2B.

In the rotating part 102, a rotary base 110 is equipped with the X-ray tube, the X-ray detector and a high-voltage generator. The rotary base 110 is arranged on a fixed base 112 through the intermediary of a bearing 111.

A drive motor 113 for rotating the rotating part 102, and electric components 114a to 114c, such as baseplates and power circuits, for controlling a dose of X-ray and other parameters are arranged on the fixed base 112. Due to the weightiness of the drive motor 113, it is disposed on a lower part of the frame 100. The electric components 114a, 114b are arranged on both shoulders of the frame 100, while the component 114c is provided on the lower part of the frame 100. Thus, as a natural result of the above-mentioned arrangement of the electric components 114a, 114b on both shoulders of the frame 100, a cover 117 for covering the whole of the frame 100 is shaped in the form of a box.

The fixed base 112, the drive motor 113 and the electric components 114a to 114c constitute a fixed part of the apparatus. By a stand 115 through tilting supports 116, the fixed part is carried so as to tilt by predetermined angles. Owing to this arrangement, it is possible for the whole frame 100 to tilt about the supports 116 as fulcrums by the predetermined angles, thereby allowing the apparatus while tilting the frame 100 to scan the patient.

From FIG. 2B where the frame 100 is viewed from its wiring side, it will be understood that a power line 120 approaches the interior of the apparatus by way of the backside of the frame 100. This is because the not-shown bed for mounting the patient is provided on the front side of the frame 100.

The power line 120 is connected to the rotating part 101 and the electric components 114a to 114c of the fixing part through the intermediary of various kinds of breakers and electric filters in the stand 115. Of course, in the rotating part 110, the electric power is supplied to the high-voltage generator and the X-ray detector through so-called "slip rings" (not shown).

Next, a signal line 121 for transmitting various control signals from console units or the like is wired by the way of the backside of the frame 100, as similar to the above-mentioned power line 120. Being wired side by side with the power line 120 as shown in FIG. 2B, the signal line 121 is also connected to the electric components 114a to 114c. Further, the signal line 121 for transmitting signals processed by the electric components 114a to 114c is divided into a signal branch line for controlling the drive motor 113 and signal branch lines for controlling the action of the bed and the X-ray system. It is noted that radiographic (pick-up) signals generated by the X-ray detector are transmitted to the console units through optical transmitting parts arranged in the rotating part 102 and the fixed part.

By the way, it should be noted that the X-ray CT apparatus and the other medical instruments have been developed in performance for recent years and their applications have been enlarged with the improvement of performance. Additionally, being involved in an information-oriented society, the above-mentioned medical instruments have been subjected to the application of electronic instruments, such as moving telephones.

Therefore, there has been caused a problem that the medical instruments operate erroneously due to radio waves and noises produced from the electronic instruments. Under such a situation, it is eagerly required to prevent the noise from generating from the medical instruments and avoid their erroneous operation.

In the above-mentioned prior art X-ray CT apparatus, however, it has a problem of increasing the length of wiring since the power line 120 and the signal line 121 have to be wired to various parts through the stand 115 and the supports 110 in order to allow the tilting operation of the frame 100. Consequently, there is a possibility of picking up unnecessary internal and external radio waves or noises due to the electrical wiring of the power line 120 and the signal line 121 etc. acting as antennas. Thus, the longer the wiring length of the medical instrument becomes, the broader the instrument can pick up the radio waves and the noises disadvantageously. Especially, since there is established a severe standard about the electromagnetic noise in IEC (international electrotechnical comission) standard which is an international standard for electrical instruments, it is required to take strong measures to cope with the IEC standard.

In addition, since the electric components 114a to 114c of the prior art X-ray CT apparatus are dispersed in the frame 100, it is difficult to take the measures for electromagnetic noise and the assembling process is apt to be complicated. Further, in assembling of the apparatus, the arrangement of the electric components 114a to 114c requires spaces for the establishment of the components 114a to 114c. Thus, the conventional X-ray CT apparatus has a problem that it is large-sized due to the frame 100 in the form of a box. Such a large-sized apparatus is apt to overawe the patient to be inspected and makes it difficult to ensure a space required for establishing the apparatus in a hospital.

Figure 3:
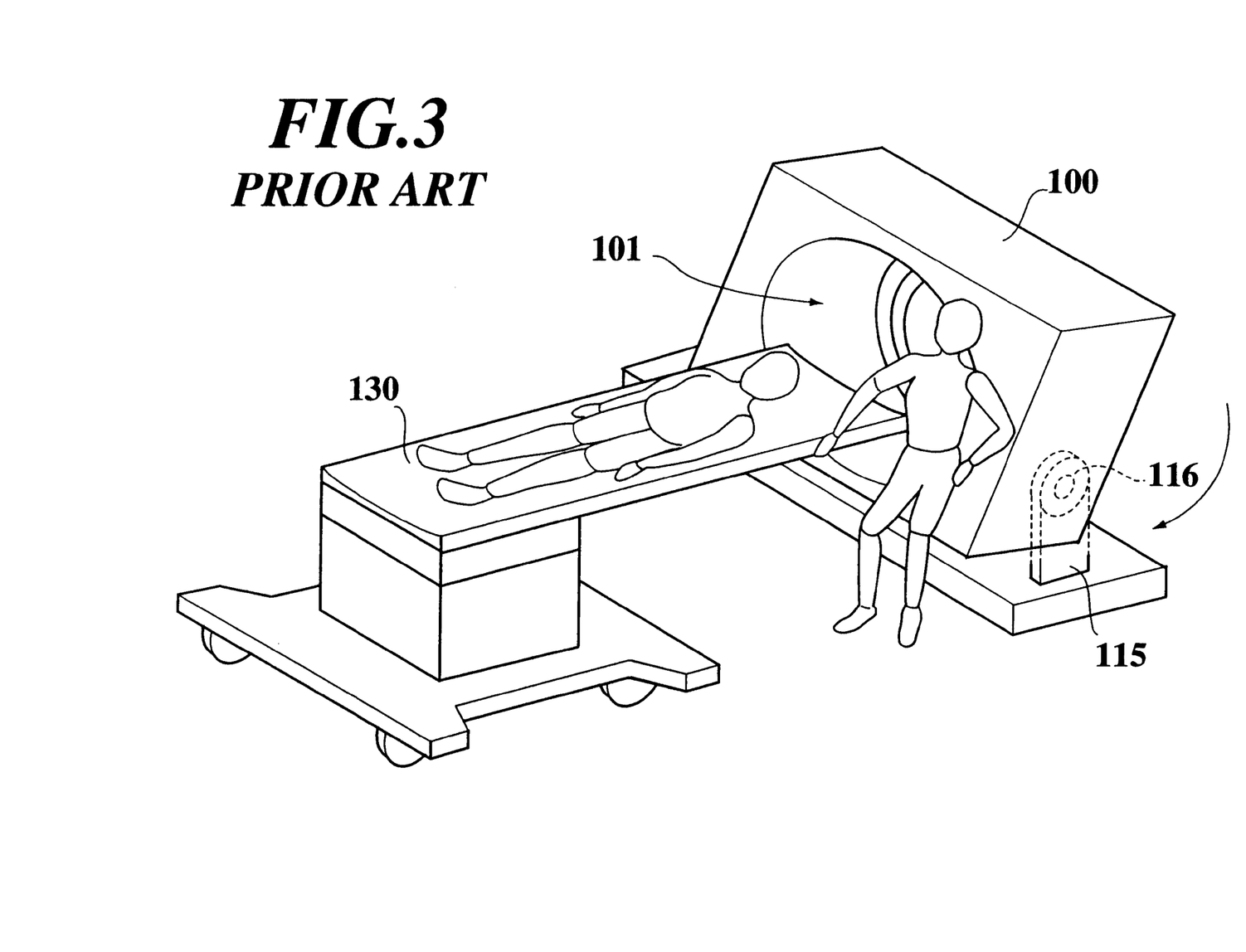
FIG. 3 is an explanatory diagram of the tilting operation of the conventional art X-ray CT apparatus.

When taking the tomography image of the patient by the oblique scanning in the conventional X-ray CT apparatus, the whole frame 100 is tilted as shown in FIG. 3. In such a case, there is a possibility that an operator's operations to adjust the position of the patient and to puncture etc. are interrupted by the projecting lower part of the slanted frame 100, thereby causing a great hindrance to the operator working about the apparatus.

SUMMARY OF THE INVENTION

It is therefore an object of the present invention to provide an X-ray CT apparatus which is capable of taking strong measures for electromagnetic noise and making the apparatus itself to be small-sized. It is an additional object of the present invention to provide an X-ray CT apparatus which is also capable of preventing the frame having the lower part projected forward by the tilting operation, from disturbing the working of the operator. These objects of the present invention described above can be accomplished by an X-ray CT apparatus comprising: a frame having a substantially circular radiographic port formed so as to allow an object to be inspected laid on a bed to be inserted thereinto; a radiographic unit accommodated in the frame, for taking a tomographic image of the object to be inspected inserted into the radiographic port; and electric components collectively positioned in a lower part of the frame; wherein at least an upper portion of the frame is so shaped as to be generally semicircular in a front view thereof.

That is, the above frame having the upper portion in the form of a substantial semicircle can be realized by shaving both shoulder portions of the conventional rectangular frame. It is noted that there exists a prior art X-ray CT apparatus having such a frame provided with a rounded upper portion; nevertheless the electric components, which would be accommodated in the shoulder portion in the conventional rectangular frame, are arranged out of the frame.

On the contrary, according to the present invention, almost electric components are positioned in the lower part of the frame collectively.

Consequently, in aspects of reliability, such a positioning of the electric components makes it easy to realize a shielding structure for the components against the electromagnetic noises. Additionally, it is possible to arrange the power line and the signal line in a perfectly separated manner and reduce the wiring area and length of the lines. Moreover, the so-shortened lines can prevent a voltage from dropping thereby to improve the reliability of the X-ray CT apparatus.

In aspects of cost, since the amount and length of wiring can be reduced by positioning the electric components at the lower part of the frame, it is possible to reduce the manufacturing cost of the apparatus. Further, the wiring of the power line and the signal line can be facilitated to simplify the manufacturing process.

In aspects of design, in comparison with the conventional X-ray CT apparatus having a box-shaped frame, it is possible to remove an overbearing feeling coming from the frame of the X-ray CT apparatus, so that the patient can be diagnosed without his anxiety. Further, for the purchasing department of the hospital, the impression that the X-ray CT apparatus looks compact would facilitate an introduction of the apparatus in the hospital.

In the above-mentioned arrangement of the invention, it is preferable that the X-ray CT apparatus further comprises a rotating unit accommodated in the frame, for rotating the radiographic unit about the radiographic port in order to take the tomographic image of the object to be inspected, and that the upper portion of the frame is rounded along a contour of the radiographic port.

More preferably, the frame is provided with a tilting unit for tilting the whole frame at a predetermined angle with a floor on which the X-ray CT apparatus is to be established.

For example, the above tilting unit comprises a fixed base which is accommodated in the frame and on which the radiographic unit is rotatably mounted, and a stand established on the floor, for supporting the fixed base tiltably.

More preferably, the rotating unit comprises a direct driving motor mounted on the fixed base.

According to the present invention, there is also provided an X-ray CT apparatus comprising:

a frame having a substantially circular radiographic port formed so as to allow an object to be inspected laid on a bed to be inserted thereinto;

a radiographic unit accommodated in the frame, for taking a tomographic image of the object to be inspected inserted into the radiographic port; and designated electric components collectively positioned in a lower part of the frame;

wherein the frame comprises:

a rotating part provided, at a center thereof, with the radiographic port, the rotating part being shaped so as to be substantially circular in its front view, the rotating part having the radiographic unit accommodated rotatably and a rotating unit for rotating the radiographic unit about the radiographic port; and a fixed part separated from the rotating part, the fixed part accommodating a tilting unit for tilting the rotating part at a predetermined angle with a floor on which the X-ray CT apparatus is to be established and also accommodating the designated electric components.

When executing the oblique scanning operation of the above-mentioned X-ray CT apparatus, the front vicinity of the fixed part can be ensured as a manipulating space for the operator since the only rotating part is subjected to the tilting movement independently of the fixed part. Thus, it is possible for the operator to position and insert the patient on the bed into the radiographic port with ease. Further, owing to the facilitated operation, the safety of the X-ray CT apparatus can be improved.

In the latter X-ray CT apparatus of the invention, it is preferable that the rotating part is provided, on an outer periphery thereof, with means for introducing air into the rotating part and means for discharging the introduced air out of the rotating part.

For example, the means for introducing air comprises at least one suction port which is arranged apart from the radiographic unit rotating in the rotating part.

Also in this X-ray CT apparatus, more preferably, the rotating unit comprises a direct driving motor for rotating the radiographic unit directly.

These and other objects and features of the present invention will become more fully apparent from the following description and appended claims taken in conjunction with the accompany drawing.

DESCRIPTION OF THE PREFERRED EMBODIMENT

Embodiments of the present invention will be described with reference to the accompanying drawings hereinafter.

Figure 4A:
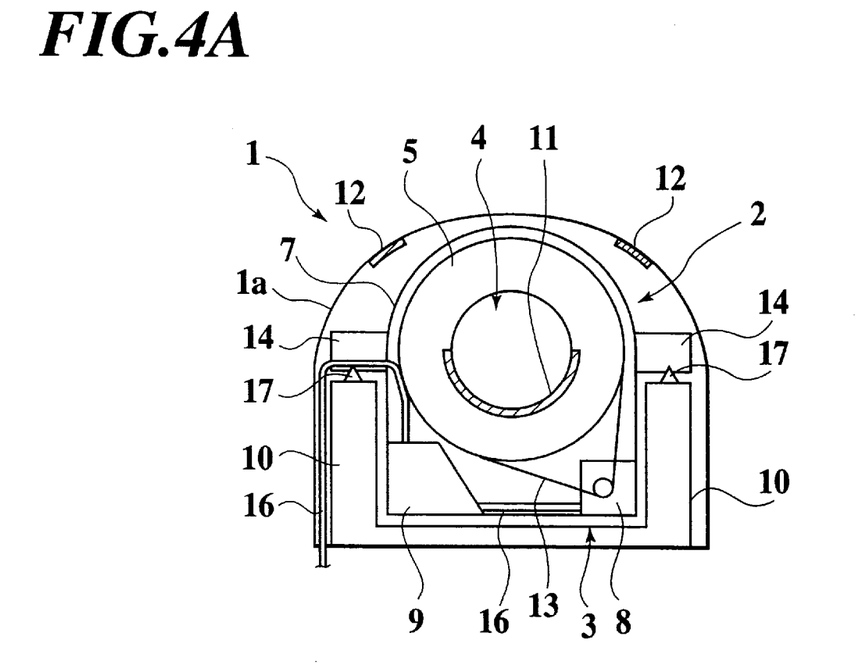
FIG. 4A is a front cross sectional view of an X-ray CT apparatus in accordance with a first embodiment of the present invention and FIG. 4B is a side cross sectional view of the X-ray CT apparatus of the first embodiment.
Figure 4B:
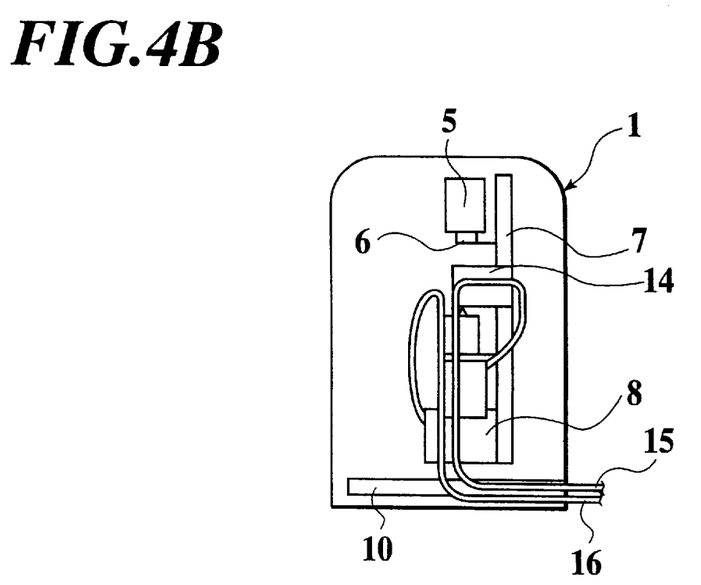
Figure 5:
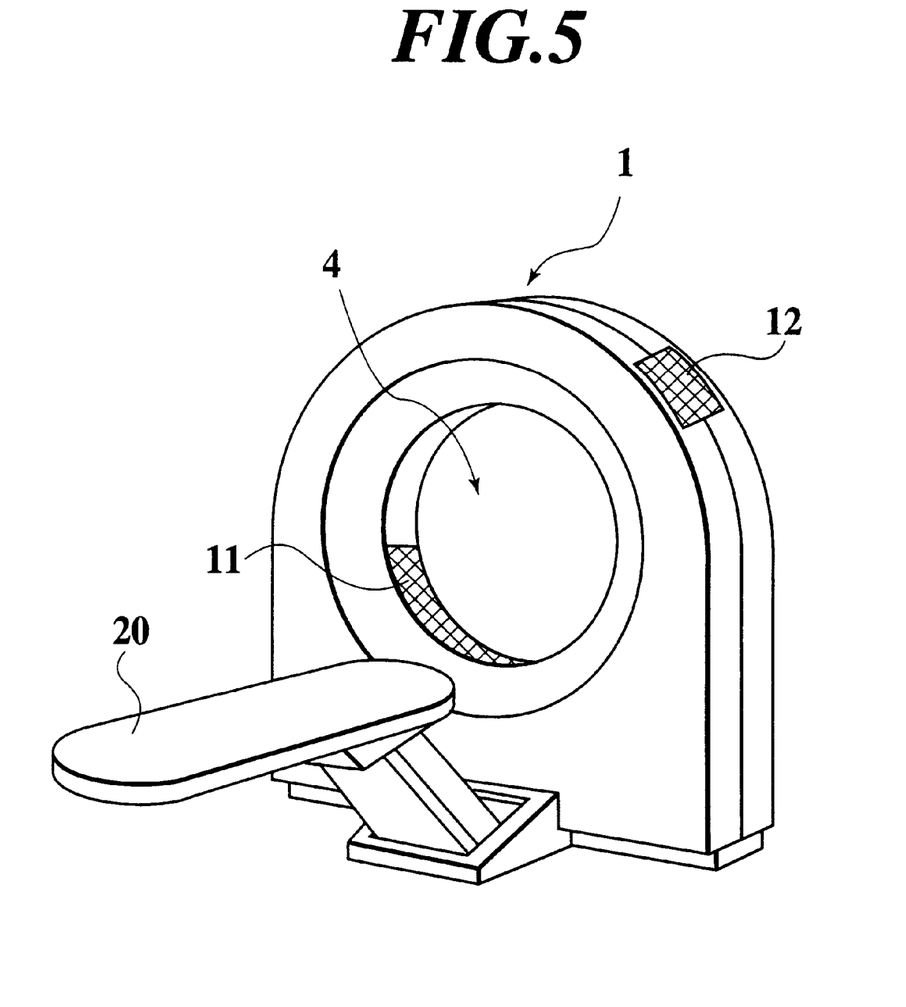
FIG. 5 is a perspective view of the X-ray CT apparatus of the first embodiment of the present invention.

First, FIG. 4A is a front cross sectional view of an X-ray CT apparatus in accordance with the first embodiment of the present invention. FIG. 4B is a side cross sectional view of the apparatus of FIG. 4A. FIG. 5 is a perspective view of the X-ray CT apparatus of the first embodiment.

The apparatus of the first embodiment, which is an X-ray CT apparatus of a so-called "helical-scanning" type, includes a rotating part 2 and a fixed part 3 in a frame 1, as shown in FIGS. 4A and 4B.

The rotating part 2 is constituted by a rotating base 5 having an X-ray tube, an X-ray detector and a high-voltage generator respectively mounted thereon. The rotating base 5 is provided, at a center thereof, with a radiographic port 4 into which a patient laid on a bed 20 (see FIG. 6A) is to be inserted. The base 5 is also arranged so as to rotate on a fixed (non-rotational) base 7 through a bearing 6. At a lower part of the fixed base 7, a drive motor 8 for rotating the rotating part 2 through the intermediary of a rotational belt 13 and electric components 9 are collectively accommodated in a magneto-proof box made of magneto-proof materials in order to take measures against electromagnetic noises. Hereat, it should be noted that the electric components 9 do not exist in both shoulder portions of the frame 1, different from the X-ray CT conventional apparatus. Therefore, a cover 1a of the frame 1 has a rounded configuration of semicircle along the rotating base 5 while deleting the conventional shoulder parts.

Note, the electric components 9 are composed of a control baseplate, an amplifier circuit system, power circuits, a timer for heaters etc., a magnet conductor for ceasing supplying the power when an overcurrent flows, fuses etc., a breaker, a control baseplate for controlling dose of X-ray or other parameters and so on. Repeatedly describing, these components 9 are gathered at the lower part of the frame 1.

Struts 14 are secured on both sides of the fixed base 7 as if they extended a diametrical line (not shown) of the fixed base 7. The struts 14 are connected to the stand 10 through tilting supports 17 so that the rotating part 2 can tilt at a predetermined angle with a floor mounting the apparatus thereon.

About the radiographic port 4 of the rotating part 2, a suction port 11 is formed to cool down heated components consisting of the X-ray tube, the high-voltage generator, the power circuit or the like, pneumatically. On the other hand, cooling fans 12 are provided on an upper face of the cover 1a, for discharging the intake air in the rotating part 2 through the suction port 11.

Figure 6A:
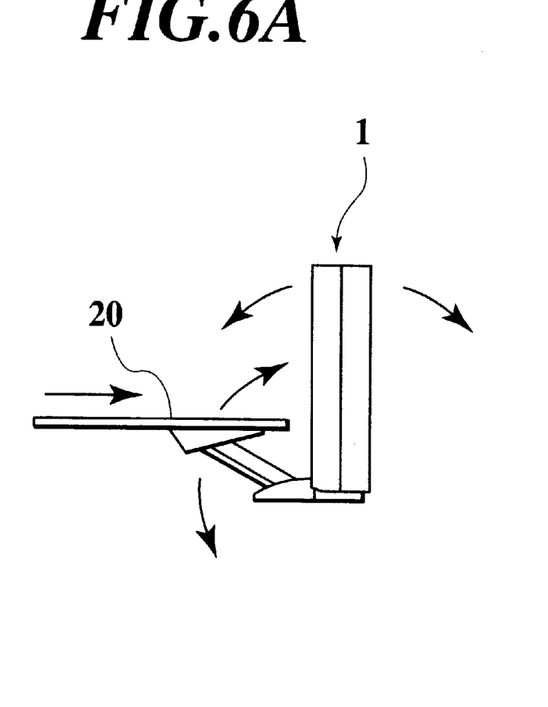
FIGS. 6A and 6B are diagrams for explanation of a tilting operation of the X-ray CT apparatus of the first embodiment.
Figure 6B:
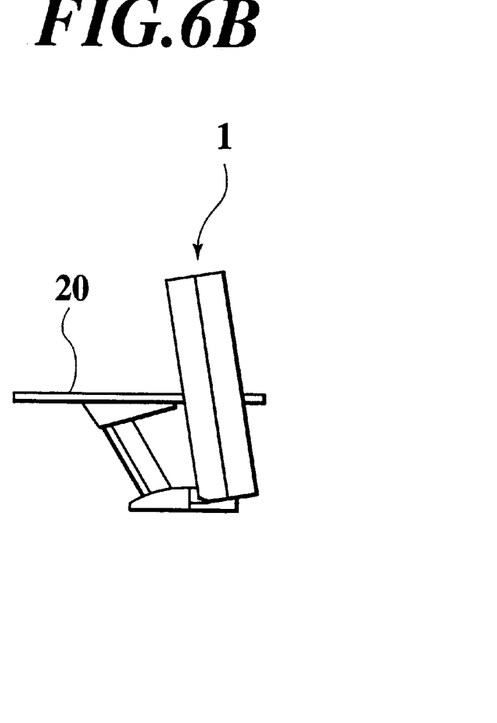

When making a diagnosis of the patient by the X-ray CT apparatus of the invention, the patient is firstly mounted on the bad 20 in order to take a tomographic image of the patient. As shown in FIG. 6A, the bed 20 is constructed so as to rise upward or fall downward within a certain range of angles and also advance at a predetermined speed. Thus, during taking the tomographic image by helical scanning, the X-ray CT apparatus controls to feed the bed 20 mounting the patient thereon at the predetermined speed and performs to irradiate the X-ray while rotating the rotating part 2. Consequently, the apparatus can irradiate the X-ray continuously in a helical manner, so that a plurality of tomographic images can be taken at a desired helical pitch. Further, not only does the apparatus perform a vertical scanning to irradiate the X-ray to the patient vertically, but the apparatus can perform an inclined scanning to irradiate the X-ray to the patient obliquely. When performing the inclined scanning, the frame 1 is slanted at a predetermined angle, as shown in FIG. 6B. In this way, it is possible to irradiate the X-ray to the patient to be inspected obliquely, thereby performing the picking-up of the inclined tomographic images.

We now describe the frame 1 from the wiring side of cables.

As shown in FIG. 4B, a power line 15 (e.g. a bundle of power cables) is arranged by way of the backside of the frame 1. This is because the bed 20 for mounting the patient has to be arranged on the front side of the frame 1, as shown in FIG. 5. The power line 15 is connected to the electric components 9 at the lower part of the frame 1 through the intermediary of various kinds of breakers and electric filters in the stand 10 and also connected to the rotating part 2 through the hollow struts 14, whereby the electric power can be supplied to various sections of the apparatus. Of course, in the rotating part 2, the electric power is supplied to the high-voltage generator and the X-ray detector through so-called "slip rings".

A signal line 16 (e.g. a bundle of signal cables) for transmitting various control signals from console units or the like is approached by the way of the backside of the frame 1, as similar to the above power line 15. Being wired side by side with the power line 15 as shown in FIG. 4B, the signal line 16 is also connected to the electric components 9 disposed at the lower part of the frame 1, as shown in FIG. 4A. Further, the signal line 16 connected to the components 9 is divided into a signal branch cable for controlling the drive motor 8 and other signal branch cables for controlling the movement of the bed 20 and controlling the operation of the X-ray system etc. It is noted that radiographic (pick-up) signals generated by the X-ray detector are transmitted to the console units through optical transmitting parts arranged in the rotating part 2 and the fixed part 3.

Hereat, it is noted that since the prior art X-ray CT apparatus has the electric components dispersed on all sides of the frame in the form of a box, the wiring of the power and signal lines are apt to be complicated and lengthened disadvantageously. On the contrary, according to the X-ray CT apparatus of the embodiment, since the electric components 9 are gathered in the vicinity of the lower part of the frame 1, it is possible to constitute the electric components 9 as one or two units and arrange the power line 15 and the signal line 16 in the form where they are perfectly separated from each other. In addition, such an arrangement of the electric components 9 allows the power line 15 and the signal line 16 to be shortened. Therefore, by constituting the electric components 9 as one or two units and reducing the lengths of the power and signal lines 15 and 16, it is possible to prevent the X-ray CT apparatus from picking up the radio waves and noises, strongly.

Furthermore, the arrangement of the electric components 9 at the lower part of the frame 1 permits the top part of the frame 1 to be rounded in the form of a semicircle, whereby the X-ray CT apparatus can be small-sized, light-weighted and low-costed. Thus, since there is no need to prepare a rigid member for a frame for supporting the rotating part 2, it is possible to provide the low-priced and light X-ray CT apparatus. Different from the conventional frame in the form of a box, such a rounded frame 1 allows the patient to be inspected at ease without being overawed. In the hospital, owing to the provision of the small-sized X-ray CT apparatus, there is no difficulty to ensure a space for setting the X-ray CT apparatus, thereby allowing it to be positioned in any consulting room etc.

In conclusion, in aspects of reliability, since almost all of the electric components in the control system can be collected in the lower part of the frame 1, it is possible to reduce and shorten the power line 15 and the signal line 16, which have been complexly wired among the components in the conventional X-ray CT apparatus, whereby the voltage drop can be restricted to improve the reliability of the apparatus. Further, it is possible to separate the signal line 15 from the power line 16 perfectly, thereby taking a firm stand against the noises. Moreover, owing to the gathered arrangement of the electric components at the lower part of the frame 1, it is easy to accomplish a shielding structure against the electromagnetic noises in the apparatus.

In aspects of design, it is possible to remove an overbearing feeling coming from the frame 1 of the X-ray CT apparatus, so that the patient can be diagnosed without his anxiety. Further, for the purchasing department of the hospital, the impression that the X-ray CT apparatus looks compact would facilitate an introduction of the apparatus in the hospital.

In aspects of cost, since the amount and length of wiring can be reduced by gathering the electric components 9 at the lower part of the frame 1, it is possible to reduce the manufacturing cost of the apparatus. Further, the wiring of the power line 15 and the signal line 16 can be facilitated to simplify the manufacturing process.

As shown in FIGS. 4A and 5, the X-ray CT apparatus of the first embodiment is provided with the suction port 11 and the cooling fans 12 as the discharging ports. Since the electric components of the X-ray CT apparatus are collected at the lower part of the frame 1, the suction port 11 is positioned at a lower semicircular part of the radiographic port 4. The cooling fans 12 are disposed on the semicircular top part of the frame 1.

Figure 7:
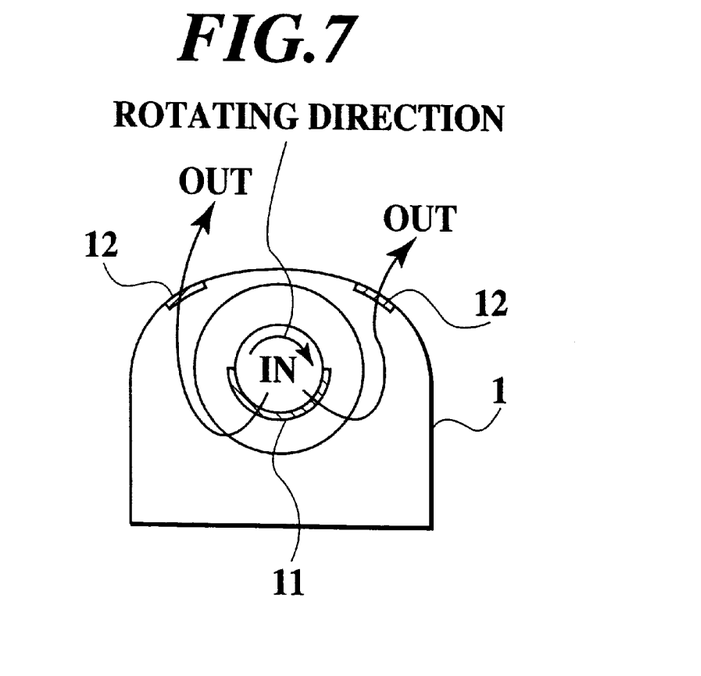
FIG. 7 is a diagram for explanation of an air-cooling function of the X-ray CT apparatus of the first embodiment.

With the above-mentioned arrangement, as shown in FIG. 7, the fresh air is sucked into the frame 1 through the suction port 11 due to the rotating action of the rotating part 2, while the air circulating in the frame 1 is discharged to the outside through the cooling fans 12. Consequently, it is possible to pneumatically cool down the electric components in the frame 1, so that the erroneous operation of the components etc. can be prevented.

We now describe the X-ray CT apparatus in accordance with the second embodiment of the invention. In the aforementioned X-ray CT apparatus of the first embodiment, the power of the drive motor 8 is transmitted to the rotating base 5 through the belt 13. On the contrary, according to the second embodiment of the invention, the rotating base 5 of is directly driven by a so-called "D.D.(direct drive) motor". Note, since the only provision of the D.D. motor differentiates the second embodiment from the first embodiment, only the difference will be explained in detail while deleting the overlapping portions between the first and second embodiments.

Figure 8A:
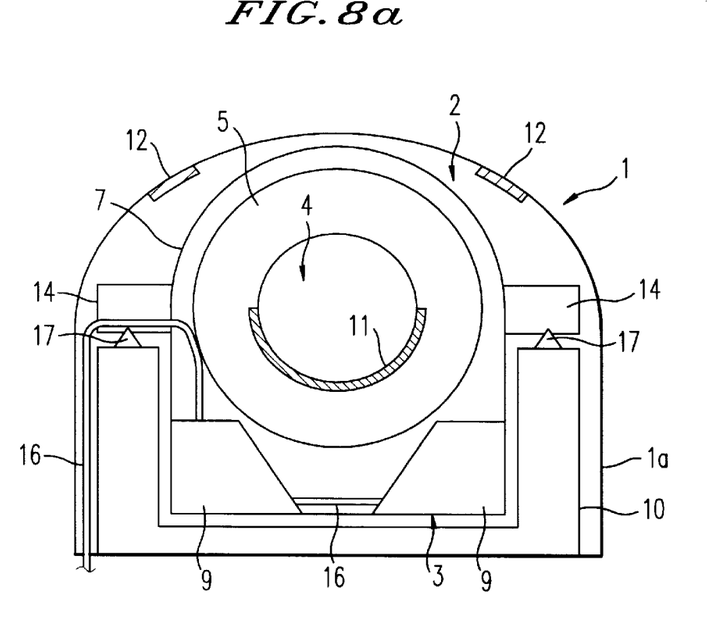
FIG. 8A is a front cross sectional view of an X-ray CT apparatus in accordance with a second embodiment of the present invention and FIG. 8B is a side cross sectional view of the X-ray CT apparatus of the second embodiment.
Figure 8B:
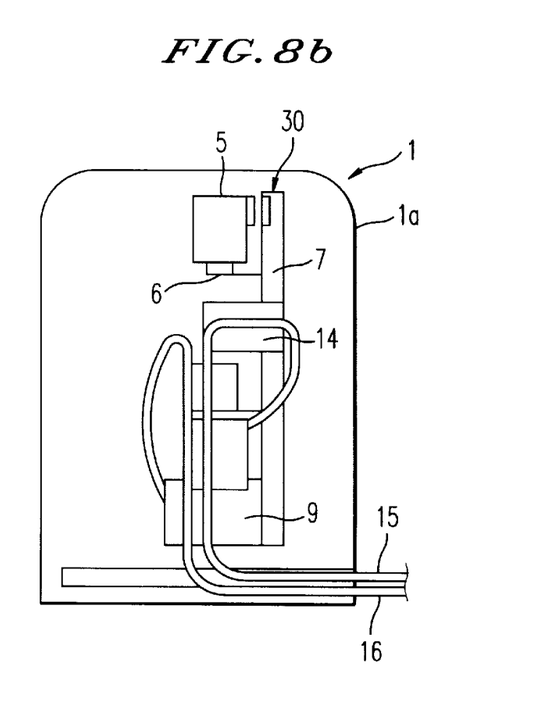

According to the second embodiment, as shown in FIG. 8B, the D.D. motor 30 is disposed between the rotating base 5 and the fixed base 7, for rotating the rotating base 5 directly.

Consequently, as shown in FIG. 8A, the provision of the D.D. motor 30 allows further electric components 9 to be also arranged in a lower position where the drive motor 8 has been arranged in the first embodiment, so that it is possible to gather almost all the electric components at the lower part of the frame 1. Therefore, it is possible to further shorten the power line 15 and the signal line 16 while separating from each other certainly, whereby the countermeasure against electromagnetic noises can be progressed furthermore. Again, besides the progressed miniaturization and lightweight of the rotating part 2, the above-mentioned effects of the X-ray CT apparatus of the first embodiment would be realized in this embodiment, too.

The third embodiment will be described hereinlater. In common with the above-mentioned first and second embodiments, the rotating part 2 and the fixed part 3 are respectively accommodated in the cover 1a and therefore, the frame 1 as a whole is slanted at the predetermined angle during the tilting operation.

On the contrary, the X-ray CT apparatus of the third embodiment comprises a rotating part and a fixed part as separated constituents. Thus, during the tilting operation of the apparatus, the rotating part is not slanted but the rotating part is solely tilted at a predetermined angle.

Figure 9A:
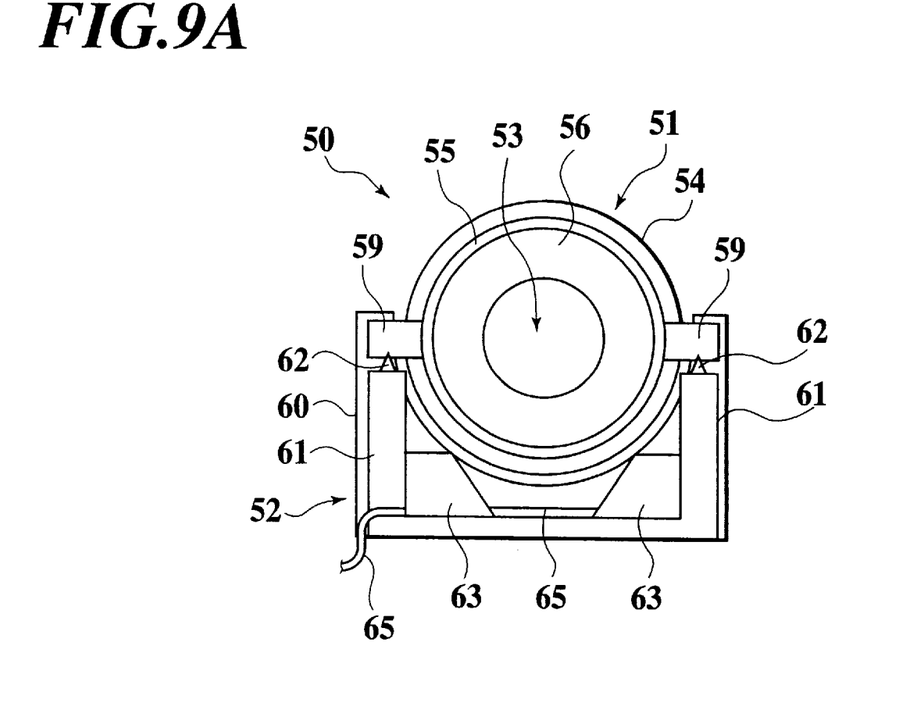
FIG. 9A is a front cross sectional view of an X-ray CT apparatus in accordance with a third embodiment of the present invention and FIG. 9B is a side cross sectional view of the X-ray CT apparatus of the third embodiment.
Figure 9B:
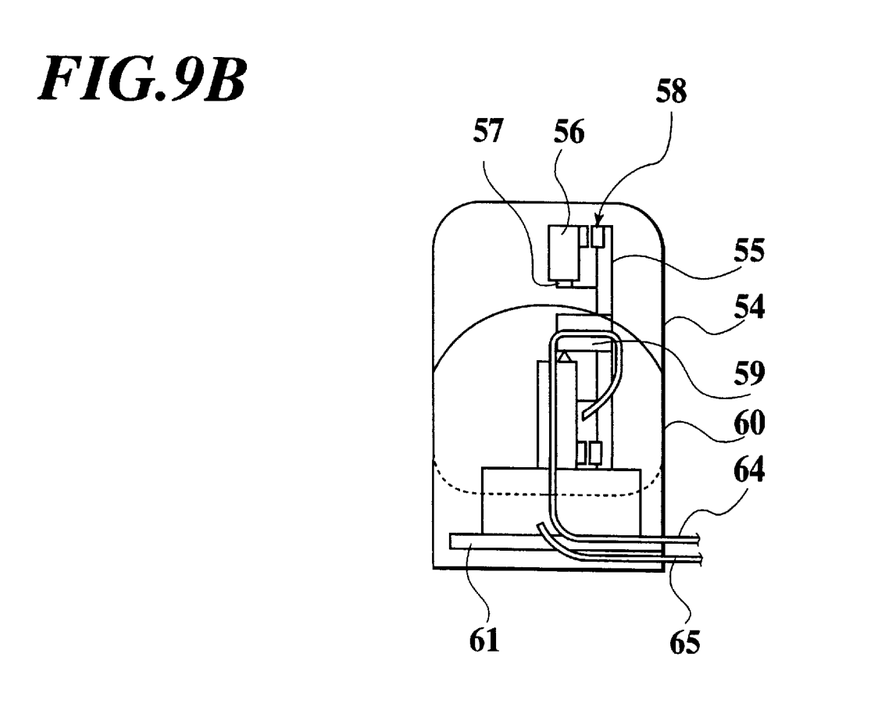
Figure 10A:
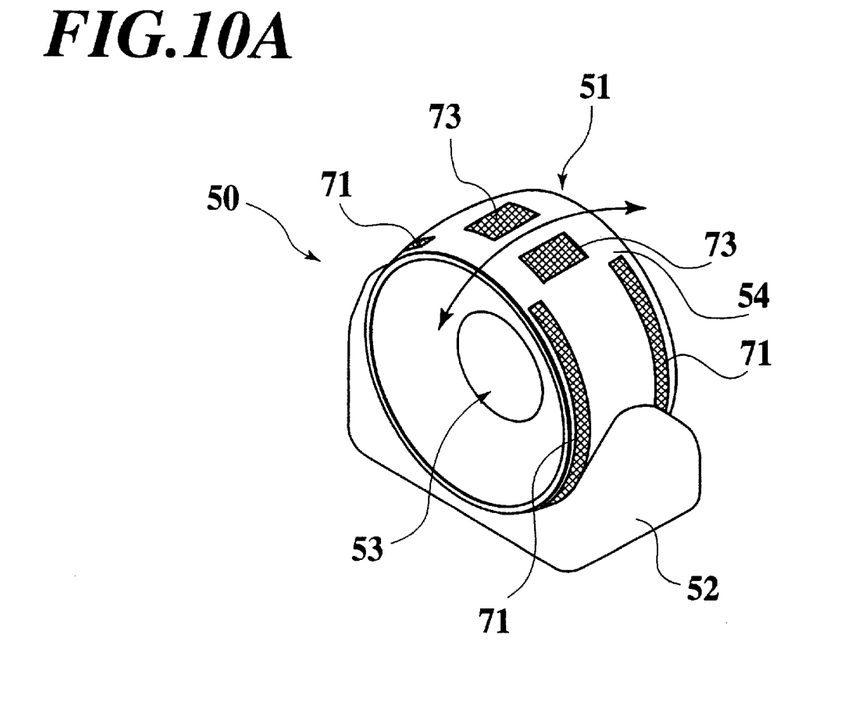
FIG. 10A is a perspective view for explanation of an air-cooling function of the X-ray CT apparatus of the third embodiment and FIG. 10B is a cross sectional view of the X-ray CT apparatus of FIG. 10A.

FIGS. 9A and 9B are front and side cross-sectional views of the X-ray CT apparatus of the third embodiments, respectively. FIG. 10A is a perspective view of the X-ray CT apparatus of the embodiment. As shown in these figures, a frame 50 of the apparatus is constituted by a rotating part 51 and a fixed part 52 for supporting the part 51, both of which are separable from each other.

In the rotating part 51, a fixed base 55 and a rotating base 56 in the form of circular discs are accommodated in a substantially cylindrical cover 54 having a radiographic port 53 into which the patient on a bed 90 (FIG. 13) is to be inserted. Therefore, the rotating part 51 looks to be circular in the front view.

The rotating base 56 is rotatably mounted on the fixed base 55 through a bearing 57. A direct driving (D.D.) motor 58 directly rotates the rotating base 56 without any intermediary such as an endless belt. On the rotating base 56, the X-ray tube, the X-ray detector and the high-voltage generator etc. are arranged so as to oppose each other. The irradiation of X-ray while rotating these elements allows the apparatus to take a tomography of the patient by helical scanning etc. Struts 59 are secured on both sides of the fixed base 55 as if they extended a diametrical line of the fixed base 55. The rotating part 51 is carried on the fixed part 52 through the struts 59 so that the part 51 can tilt at a predetermined angle, through it will be described later.

In the fixed part 52, a stand 61, supports 62 and electric components 63 are collectively accommodated in a fixed cover 60 having a concave portion in the front view. Together with the stand 61, the supports 62 serve to carry the rotating part 51 tiltably. For example, the electric components 63 are composed of a control baseplate, an amplifier circuit system, power circuits, a timer for heaters etc., a magnet conductor for ceasing supplying the power when an overcurrent flows, fuses etc., a breaker, a control baseplate for controlling dose of X-ray or other parameters and so on. These electric components 63 are collectively accommodated in a magneto-proof box made of magneto-proof materials for measuring against the electromagnetic noises.

In operation of the X-ray CT apparatus, the patient is mounted on the bed to take a tomographic image of the patient. As described with reference to FIG. 6A before, the bed 90 is constructed so as to rise upward or fall downward within a range of predetermined angles and also advance at the predetermined speed. Thus, during taking the tomographic image by helical scanning, the X-ray CT apparatus controls to feed the bed 90 mounting the patient thereon at the predetermined speed and performs to irradiate the X-ray while rotating the rotating part 51. Consequently, the apparatus can irradiate the X-ray continuously in a helical manner, so that a plurality of tomographic images can be taken at a desired helical pitch. Further, not only does the apparatus perform the vertical scanning to irradiate the X-ray to the patient vertically, but the apparatus can perform the inclined scanning to irradiate the X-ray to the patient obliquely. When it is required to perform the inclined scanning, the operator inputs a desired irradiation angle (the incident angle of X-ray) to the apparatus. Consequently, as shown in FIG. 10A, the rotating part 51 is tilted at the predetermined angle about the supports 62 of the fixed part 52 as fulcrums. In this way, it is possible to irradiate the X-ray to the patient to be inspected obliquely, thereby performing to pick up the inclined tomographic images.

According to the above-mentioned X-ray CT apparatus, since the frame 50 is constituted while separating the rotating part 51 from the fixed part 52, it is possible to provide the part 51 having a circular configuration, whereby the X-ray CT apparatus itself can be small-sized. Further, it is possible to eliminate the patient's oppressed feeling and the anxiety for installation space in the hospital as well as the cases of the previously-mentioned X-ray CT apparatuses.

When viewing the X-ray CT apparatus of the embodiment from its wiring side, as shown in FIG. 9B, it will be noted that a power line 64 is arranged by way of the backside of the fixed part 52. The power line 64 is connected to the electric components 63 in the fixed part 52 through the intermediary of various kinds of breakers and electric filters in the stand 61 and also connected to the rotating part 51 through the hollow struts 59. Of course, in the rotating part 51, the electric power is supplied to the high-voltage generator and the X-ray detector through so-called "slip rings".

As shown in FIG. 9B, a signal line 65 which transmits various control signals from console units or the like is wired by the way of the backside of the fixed part 52, as well as the power line 64. Being wired side by side with the power line 64, the signal line 65 is also connected to the electric components 63 in the fixed part 52 disposed at the lower part of the frame 1, as shown in FIG. 9A. Further, the signal line 65 connected to the components 63 is divided into a signal branch line for controlling the D.D. motor 58 and other signal branch lines for controlling the operations of the bed and the X-ray system etc. It is noted that radiographic (pick-up) signals generated by the X-ray detector are transmitted to the console units through optical transmitting parts arranged in the rotating part 51 and the fixed part 52.

Owing to the provision of the frame 50 where the rotating part 51 is separated from the fixed part 52, it is possible to separate the power line 64 from the signal line 65 certainly, thereby allowing of perfect measures against the electromagnetic noises. Since the electric components 63 etc. are arranged on the side of the fixed part 52 collectively, the weight of the rotating part 51 can be further reduced while miniaturizing the components for executing such a tilting motion. Thus, it is possible to reduce the size and weight of the whole X-ray CT apparatus while effecting the same merits as those of the previous embodiments.

Figure 10B:
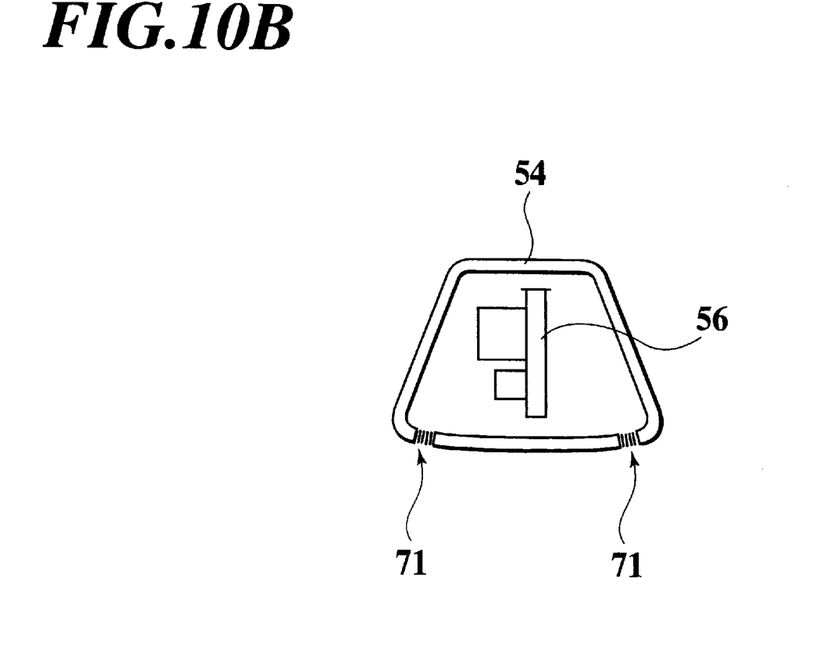

As shown in FIG. 10A, the X-ray CT apparatus of the embodiment has suction ports 71 formed along the periphery of the cover 54 of the rotating part 51 and cooling fans 73 serving the discharging ports, which are arranged on the top portion of the cover 54. On a portion of the cover 54 where no rotating member is positioned, the suction ports 71 are so formed as to extend over almost the whole circumference of the cover 54. In detail, as shown in FIG. 10B, the suction ports 71 are formed in the vicinity of both edges of the circumferential part of the cover 54. Both size and position of each orifice of the suction ports 71 are determined on calculation so that the air flowing into the cover 54 through one of the suction ports 71 does not obstruct the air flow flowing into the cover 54 through the other suction port 71, that is, in view of accomplishing flowing distribution suitable for air-cooling.

In the X-ray CT apparatus, the air introduced through the suction ports flows to cool down the heated components of the X-ray tube, the high voltage generator and the power circuit etc. in the rotating part 51 and thereafter, the air is discharged outside the rotating cover 54 through the cooling fans 73.

Repeatedly, in case of the conventional X-ray CT apparatus of FIG. 1, it 10 should be noted that it has been necessary to provide the suction ports 103 on the bottom part 100a of the frame 100 because of its box-shaped configuration. Therefore, there has been a problem that the heated air to be discharged is apt to stagnate in the frame 100. Even if suction ports were formed on lateral sides of the frame 100, it would be difficult to effect the smooth inhalation of air due to the obstacles in the frame 10 and its box-shaped configuration per se.

On the contrary, according to the X-ray CT apparatus of the embodiment, the frame 50 is constituted by the rotating part 51 and the fixed part 52, both of which are separated from each other and associated with each other at the struts 59 alone. Thus, the circumference of the cover 54 of the rotating part 51 is substantially released to the outside. Such a released arrangement of the cover 54 allows the suction ports 71 to be formed over the whole circumference of the cover 54 nearly, whereby it is possible to improve the cooling capability of the apparatus with an increased inhalation of the air into the cover 54.

Again, if one or more suction ports are formed in the vicinity of the rotating elements in the cover 54, an air current urging the inside air to the outside will be produced by the centrifugal force of the rotating elements (e.g. the rotating base 56), so that it would be difficult to carry out the smooth inhalation through the suction port. However, according to the embodiment, since the suction ports 71 are positioned in the cover-portions having no rotating element arranged in the neighborhood, it is possible to realize the smooth inhalation under no influence of the centrifugal force of the rotating base 56 and so on.

Accordingly, the X-ray CT apparatus allows the heated components to be cooled down effectively, whereby the safety and reliability of the apparatus can be progressed.

Although two suction ports 71 are provided on both sides of the cover 54 in the above-mentioned embodiment, a single suction port may be arranged on either side 4 or in the center of the cover 54 in the modification. Alternatively, the cover 54 may be provided with three suction ports on both sides and center of the periphery of the cover 54. In case of a single suction port on the cover 54, then it will be possible to delete the aforementioned calculation for flowing distribution.

Figure 11:
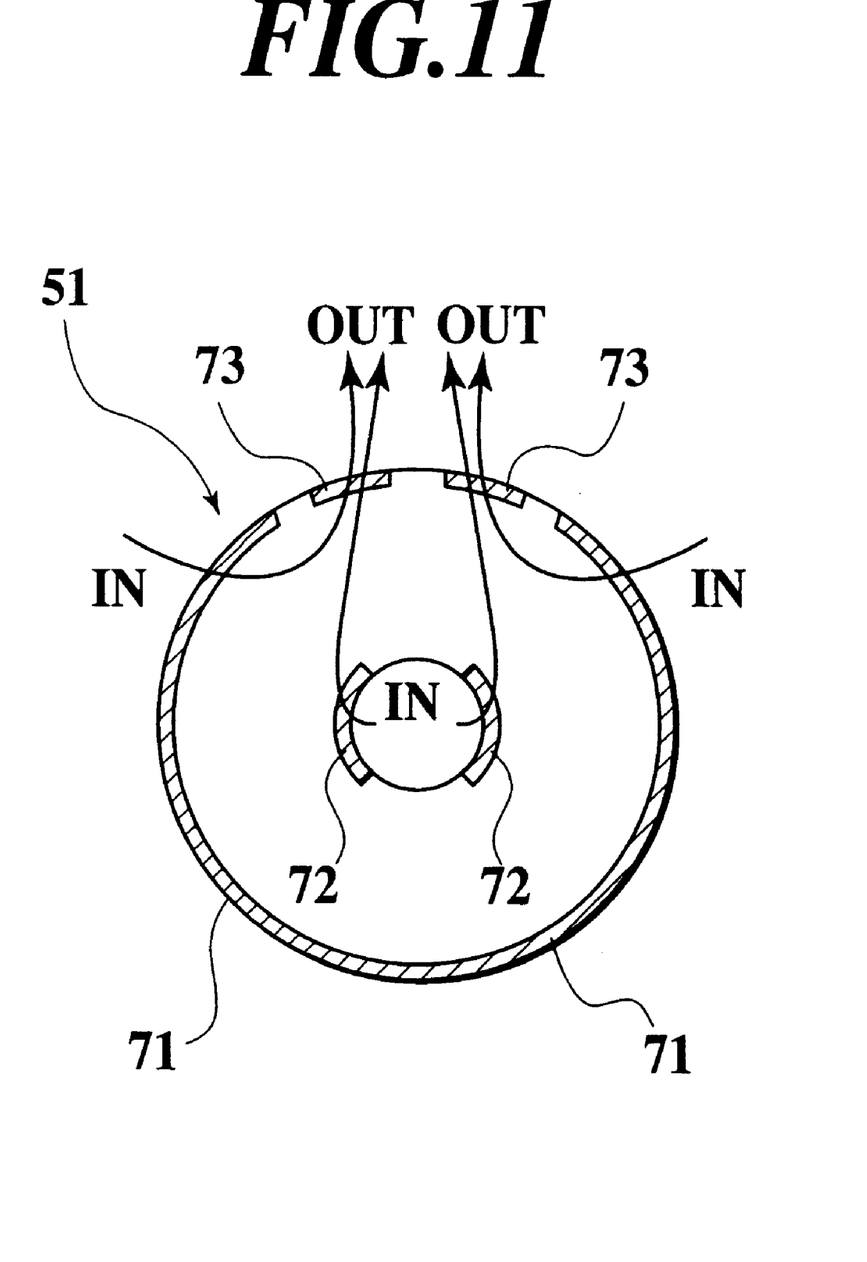
FIG. 11 is a cross sectional view for explanation of an air-cooling function of the X-ray CT apparatus in a modification of the third embodiment of the present invention.

In a further modification, not only does the cover 54 have the suction ports formed on the outer periphery, but the cover 54 has suction ports arranged on the inner periphery, as indicated with reference numerals 72 of FIG. 11. In this case, the fresh air introduced through the suction ports 71 and 72 operates to cool down the heated components, for example the X-ray tube, the high-voltage generator, the power circuit etc., in the rotating part 51 and thereafter, the air is discharged to the outside via. the cooling fans 73 on the top part of the cover 54. With the arrangement of the suction ports 71, 72, it is possible to cool down the heated components effectively, whereby the safety and reliability of the apparatus can be improved as similar to the previous embodiments.

Figure 12:
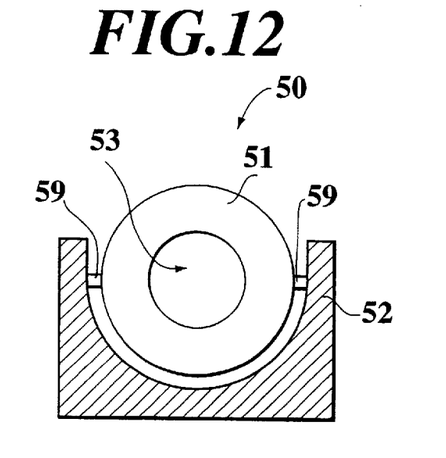
FIG. 12 is a view showing a tilting structure of the X-ray CT apparatus of the third embodiment.
Figure 13:
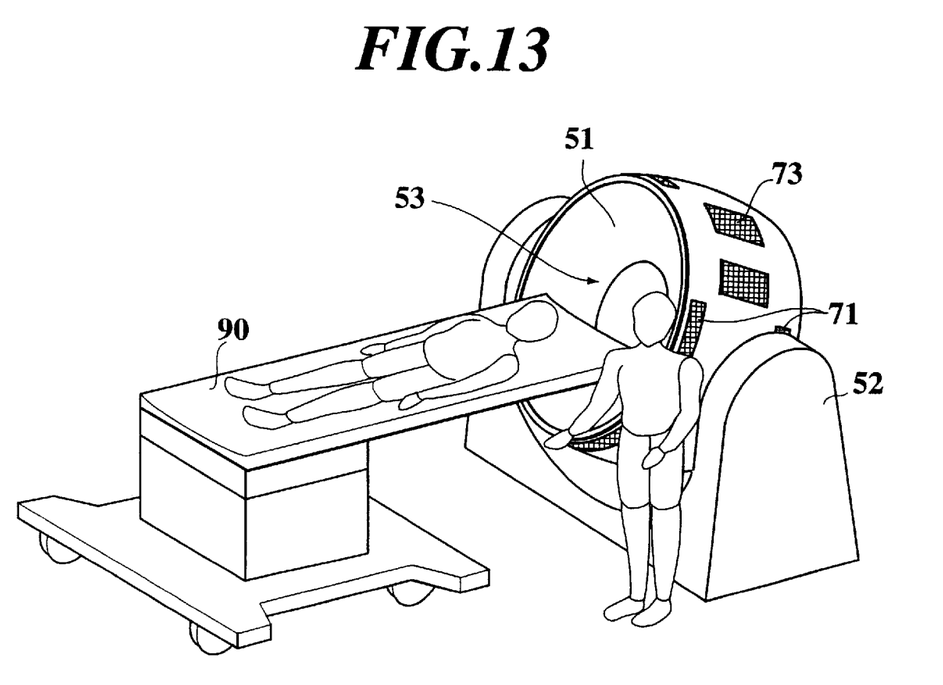
FIG. 13 is an explanatory diagram of the tilting operation of the X-ray CT apparatus of FIG. 12, showing a situation where the apparatus does not disturb the operator.

In the X-ray CT apparatus of the third embodiment, as shown in FIG. 12, the frame 50 is constituted by the circular rotating part 51 and the fixed part 52 supporting the part 51 at the supports 59 rotatably, which is indicated with slanted lines in the figure. When taking the tomography of the patient by oblique scanning in the so-constructed frame 50, the rotating part 51 alone is tilted with respect to the fixed part 52, as shown in FIG. 13.

Hitherto, in case of tilting the whole frame, the operator has been interrupted by the projecting frame, thereby hindering the operator's work to position and insert the patient. On the contrary, according to the embodiment, the front vicinity of the fixed part 52 can be ensured as a manipulating space for the operator since the only rotating part 51 is subjected to the tilting movement independently of the fixed part 52. Thus, it is possible for the operator to easily position and puncture the patient. Further, owing to the facilitated operation, the safety of the X-ray ct apparatus can be improved.

Finally, it will be understood by those skilled in the art that the foregoing description is merely related to a few of embodiments of the X-ray ct apparatus, and that various changes and modifications may be made to the present invention without departing from the spirit and scope thereof.

What is claimed is:

1. An X-ray CT apparatus comprising;
    a frame having a substantially circular radiographic port formed so as to allow an object to be inspected laid on a bed to be inserted thereinto;
    a radiographic unit accommodated in the frame, for taking a tomographic image of the object to be inspected inserted into the radiographic port; and
    electric components collectively positioned in a lower part of the frame, said electric components including at least a control baseplate, an amplifier circuit system, power circuits, a timer for heaters, a magnet conductor for ceasing supplying power when an overcurrent flows, fuses, a breaker, and a controller for controlling dose of X-ray or other parameters.

2. An X-ray CT apparatus as claimed in claim 1, further comprising a rotating unit accommodated in the frame, for rotating the radiographic unit about the radiographic port in order to take the tomographic image of the object to be inspected, wherein the upper portion of the frame is rounded along a contour of the radiographic port.

3. An X-ray CT apparatus as claimed in claim 2, wherein the frame is provided with a tilting unit for tilting the whole frame at a predetermined angle with a floor on which the X-ray CT apparatus is to be established.

4. An X-ray CT apparatus as claimed in claim 3, wherein the tilting unit comprises:
    a base which is accommodated in the frame and on which the radiographic unit is rotatably mounted; and
    a stand established on the floor, for supporting the base tiltably.

5. An X-ray CT apparatus as claimed in claim 4, wherein the rotating unit comprises a direct driving motor mounted on the base.

6. An X-ray CT apparatus as claimed in claim 1, wherein the frame comprises:
    a rotating part provided, at a center thereof, with the radiographic port, the rotating part being shaped so as to be substantially circular in its front view, the rotating part having the radiographic unit accommodated rotatably and a rotating unit for rotating the radiographic unit about the radiographic port; and
    a fixed part separated from the rotating part, the fixed part accommodating a tilting unit for tilting the rotating part at a predetermined angle with a floor on which the X-ray CT apparatus is to be established and also accommodating the designated electric components.

7. An X-ray CT apparatus as claimed in claim 6, wherein the rotating part is provided, on an outer periphery thereof, with means for introducing air into the rotating part and means for discharging the introduced air out of the rotating part.

8. An X-ray CT apparatus as claimed in claim 7, wherein the means for introducing air comprises at least one suction port which is arranged apart from the radiographic unit rotating in the rotating part.

9. An X-ray CT apparatus as claimed in claim 8, wherein the rotating unit comprises a direct driving motor for rotating the radiographic unit directly.

10. An X-ray CT apparatus as claimed in claim 1, wherein at least an upper portion of the frame is so shaped as to be generally semicircular in a front view thereof.

11. An X-ray CT apparatus as claimed in claim 1, wherein said lower part of said frame comprises a box having electromagnetic shielding and in which said electrical components are accommodated.

12. An X-ray CT apparatus according to claim 4, comprising:
    a first cover surrounding said fixed base; and
    a second cover separate from said first cover surrounding said rotatably mounted radiographic unit.

13. An X-ray CT apparatus according to claim 1, comprising:
    a cover surrounding said radiographic unit;

an air discharging port and an air suction port arranged on a side face of the cover and on an inner face of the cover in front view, respectively.

14. An X-ray CT apparatus according to claim 4, comprising:

a cover surrounding said radiographic unit;

an air discharging port and an air suction port arranged on a side face of the cover and on an inner face of the cover in front view, respectively.

15. An X-ray CT apparatus according to claim 13, comprising:

an air suction port arranged on a side face of the cover.

16. An X-ray CT apparatus according to claim 14, comprising:

an air suction port arranged on a side face of the cover.

* * * * *